(12) United States Patent
Drobnik et al.

(10) Patent No.: US 8,834,340 B2
(45) Date of Patent: Sep. 16, 2014

(54) RADIATION CONTAINING SEEDS AND METHOD FOR HIGH VISIBILITY MAGNETIC IMAGING

(75) Inventors: Christopher D. Drobnik, Wauconda, IL (US); Michael W. Drobnik, Downers Grove, IL (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 13/524,763

(22) Filed: Jun. 15, 2012

(65) Prior Publication Data

US 2012/0253177 A1 Oct. 4, 2012

Related U.S. Application Data

(63) Continuation of application No. 12/371,004, filed on Feb. 13, 2009, now abandoned.

(60) Provisional application No. 61/030,735, filed on Feb. 22, 2008.

(51) Int. Cl.
*A61M 36/00* (2006.01)
*A61N 5/10* (2006.01)
*A61B 5/055* (2006.01)

(52) U.S. Cl.
CPC ........ *A61N 5/1027* (2013.01); *A61N 2005/1024* (2013.01); *A61B 5/055* (2013.01)
USPC .................................. 600/8; 600/3; 600/411

(58) Field of Classification Search
CPC .............. A61N 5/1001; A61N 5/1027; A61N 2005/1001; A61N 2005/1024
USPC ........................................................ 600/1–8
See application file for complete search history.

(56) References Cited

U.S. PATENT DOCUMENTS

| | | | |
|---|---|---|---|
| 4,323,055 A | 4/1982 | Kubiatowicz | |
| 5,342,283 A * | 8/1994 | Good | 600/8 |
| 6,200,258 B1 * | 3/2001 | Slater et al. | 600/8 |
| 2002/0162828 A1 * | 11/2002 | Spooner et al. | 219/121.63 |
| 2003/0092957 A1 | 5/2003 | Scott et al. | |
| 2005/0101826 A1 * | 5/2005 | Bray et al. | 600/8 |
| 2009/0216065 A1 | 8/2009 | Drobnik et al. | |

OTHER PUBLICATIONS

Kirov, Assen S., Jeffrey F. Williamson. "Monte Carlo-aided dosimetry of the Source Tech Medical Model STM1251 I-125 interstitial brachytherapy source." Medical Physics 28.5 (May 2001): 764-772.*
ASTM International, "Standard Specification for Autocatalytic (Electroless) Nickel-Phosphorous Coatings on Metal," B 733-04, Aug. 2004.
U.S. Appl. No. 12/371,004, filed Feb. 13, 2009 Non-Final Office Action dated Feb. 29, 2012.

* cited by examiner

*Primary Examiner* — Charles A Marmor, II
*Assistant Examiner* — Carrie R Dorna
(74) *Attorney, Agent, or Firm* — Rutan & Tucker, LLP

(57) ABSTRACT

A radioactive seed and method for making a radioactive seed with selective magnetic imaging characteristics are provided. The seed includes a housing which may include a metal shell for at least partially enclosing a radioactive material. The shell encloses a rod having a nickel layer with a phosphorous content, wherein the phosphorous content includes a level of phosphorous sufficient, when the seed is implanted in tissue, to provide a magnetic resonance image of the seed while substantially eliminating gross artifacts in the magnetic resonance image.

17 Claims, 1 Drawing Sheet

RADIATION CONTAINING SEEDS AND METHOD FOR HIGH VISIBILITY MAGNETIC IMAGING

PRIORITY

This application is a continuation of U.S. patent application Ser. No. 12/371,004, filed Feb. 13, 2009, which claims the benefit of priority to U.S. Provisional Application No. 61/030,735, filed Feb. 22, 2008, each of which is incorporated by reference in its entirety into this application.

TECHNICAL FIELD

The invention relates generally to radioactive seeds and more particularly to radioactive seeds formulated for improved magnetic resonance imaging.

BACKGROUND

Bodily cancers are commonly treated using radiation therapy. Radiation therapy employs high energy radiation to kill cancer cells. One type of radiation therapy is brachytherapy, in which a source of radiation is in direct contact with an afflicted tissue. A common brachytherapy treatment, transperineal seed implantation, involves placing radioactive seeds in the prostate gland to kill prostate gland cancer cells. A physician employs tools, for example, ultrasound, computed axial tomography ("CAT" or "CT") scans, magnetic resonance imaging ("MRI") scans and X-ray images in concert with dose-planning computer software programs to evaluate the medical condition of a patient. The physician constructs an optimal treatment plan to evenly distribute radiation throughout the afflicted tissue. Radioactive seeds of discrete radioactive strengths are inserted into the afflicted tissue through multiple implantation needles at positions corresponding to the treatment plan.

During prostate brachytherapy, the position of the radioactive seeds in relation to the prostate gland and to adjacent structures in the body must be known to a relatively high degree of precision to accurately determine if the dose of radiation delivered from the seeds is adequate to eradicate the prostate cancer. Currently, seeds are guided into the prostate using transrectal ultrasound guidance which is good for imaging the soft tissue of the prostate and the surrounding structures. Occasionally fluoroscopy is used in conjunction with the ultrasound to provide improved images of the seeds. Following the implant, the seed position is typically determined using CT imaging. Using the determined seed positions, the dosimetry of the implant is calculated based on the obtained CT images. The CT images have been shown however to be deficit in imaging soft tissue structures, therefore, performing ultrasound imaging or MRI imaging and fusing the ultrasound or MRI images with the CT images is often performed.

Many of the current modalities have shortcomings that need to be overcome before an accurate determination of implant location can be made. For example, ultrasound can determine the structure of the gland and surrounding anatomy to a high degree of accuracy. However, ultrasound is not very accurate at imaging the seeds. Various attempts have been made to design the seeds to be more echogenic (i.e., more accurately imaged by ultrasound). The brachytherapy seed sold as ONCOSEED™, by Oncura, uses ribs on an outer titanium hull of the seed to increase its ultrasonic reflection. Other attempts have been made to incorporate gas bubbles into the walls of the seeds or into stranding material holding the seeds together to enhance the ultrasound reflection. These attempts have been minimally successful primarily due to the small target size of the seed, the background noise caused by the other seeds in the implant, the echogenic needle tracks created in the gland and the like.

Other methods for locating and imaging the seeds also have shortcomings. Fluoroscopy is very good at identifying the seeds due to the heavy metal X-ray markers in the seeds. Unfortunately, fluoroscopy is poor at imaging the soft tissue in and around the prostate gland. CT imaging is acceptable at imaging both the seeds and the soft tissues, but it is far from ideal. CT imaging is typically not refined enough to image critical structures around the gland and therefore, generally used for gross position analysis only. CT imaging is most often used to do post implant dosimetry. Studies have shown that there is a great deal of operator-to-operator variability, however, in contouring the prostate shape and size for a given image. This variability leads to subsequent variations in the determination of the adequacy of the dose delivered.

MRI imaging is the preferred method for imaging the prostate anatomy. Identification of critical structures located around the prostate gland can be performed using MRI imaging. MRI imaging is however rather poor at imaging the seed positions following an implant. Uncontrolled artifacts for the seed can also distort the gland image and make accurate dosimetry assessment difficult. In the presence of sufficient artifacts, the seeds may be invisible to MRI imaging. Additionally, the degree of artifact, or visibility, for a given seed type varies from vendor to vendor and, possibly, even from lot to lot from the same vendor.

Medical professionals therefore are required to compensate for deficits in one or more of the available imaging technologies by employing multiple imaging techniques and fusing the resulting images to determine an accurate location of the implant.

Thus, a need exists for a radioactive seed conducive to providing high fidelity during a magnetic resonance imaging procedure while reducing artifacts caused by the seed in the image.

SUMMARY

The invention in one implementation encompasses a radioactive seed manufactured to have desired magnetic characteristics. The seed may comprise a metal shell for at least partially enclosing a radioactive material. A rod traverses the shell and contains a nickel layer. The nickel layer has a phosphorus content which is sufficient, when the seed is implanted in tissue, to provide a magnetic resonance image of the seed while substantially eliminating gross artifacts in the image.

Another implementation of the invention encompasses a method for making a radioactive seed to have desired magnetic characteristics. The method may comprise providing a rod for insertion in a shell of a radioactive seed. The method may comprise the steps of: coating the rod with a nickel layer; providing incorporation of phosphorus into the nickel layer; and adjusting the concentration of the phosphorous such that when the seed is placed in tissue and a magnetic resonance image is taken thereof, a level of phosphorous in the nickel layer is sufficient to substantially eliminate gross artifacts in the magnetic resonance image while providing visibility of the seed on the magnetic resonance image.

DESCRIPTION OF THE DRAWINGS

Features of exemplary implementations of the invention will become apparent from the description, the claims, and the accompanying drawing in which:

DETAILED DESCRIPTION

Figure 1:
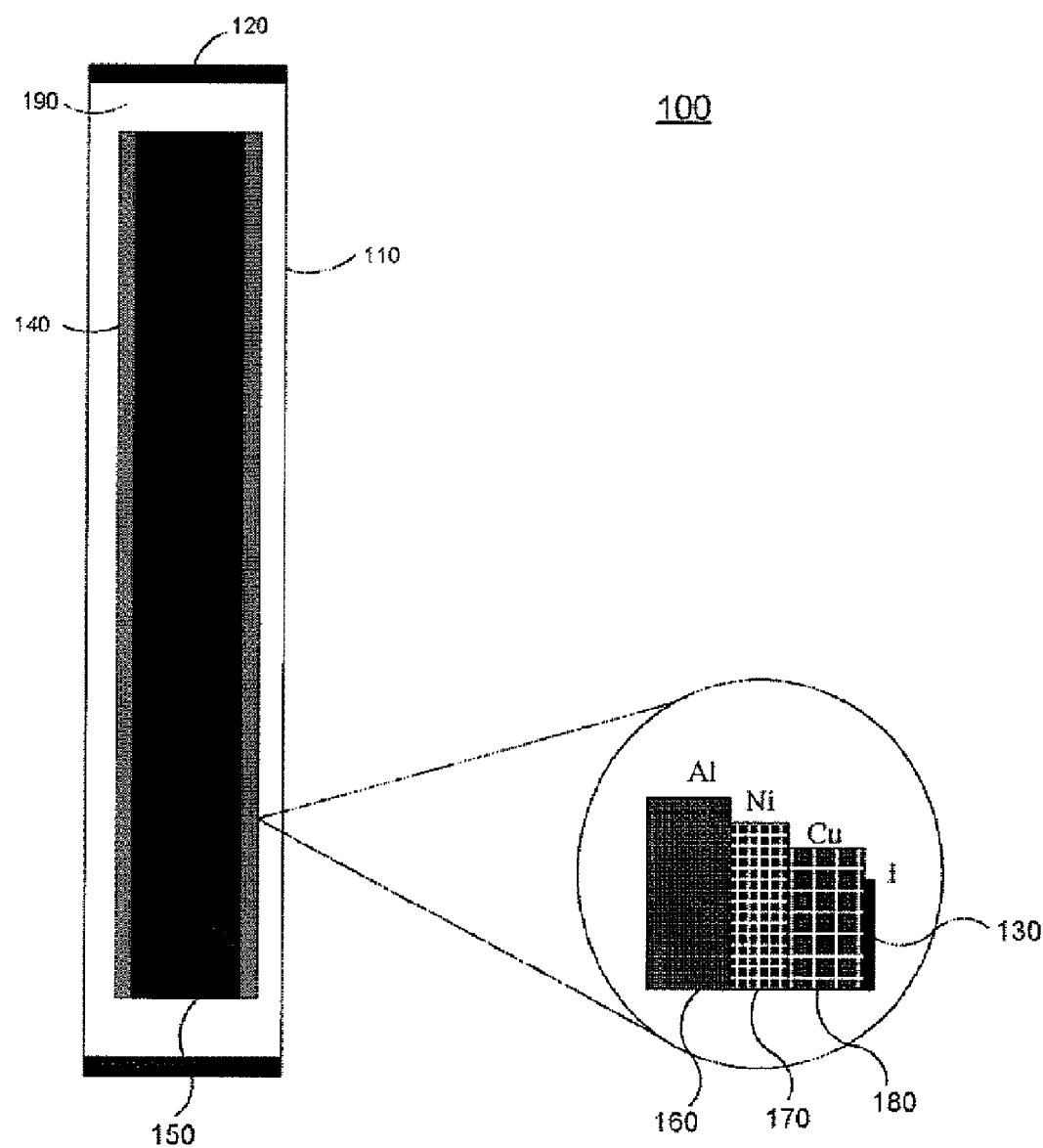
FIG. 1 is a representation of an exemplary implementation of an apparatus that comprises a radioactive seed.

While this invention is susceptible of embodiment in many different forms, there is shown in the drawing and will herein be described in detail preferred embodiments of the invention with the understanding that the present disclosure is to be considered as an exemplification of the principles of the invention and is not intended to limit the broad aspect of the invention to the embodiments illustrated.

Turning to FIG. 1, an apparatus 100 comprising a radioactive seed 110 for inserting into a prostate organ for treating, for example, prostate cancer is shown. The radioactive seed 110 in accordance with an embodiment of the invention is manufactured to have desired magnetic characteristics. The seed 110 comprises a metal shell 120 that encloses, at least partially, a radioactive material 130. The radioactive material 130 is used to irradiate cancers in a well known manner. The metal shell 120 may be comprised of any appropriate material, such as titanium. The radioactive seed 110 further comprises a rod 140 traversing the shell 120. The metal shell 120 and the rod 140 may comprise a housing for at least partially enclosing the radioactive material. The rod 140 may be made of a number of layers. For example, the rod 140 may comprise a gold core 150 surrounded by a layer of aluminum 160. The layer of aluminum 160 may be surrounded by consecutive layers of nickel 170, copper 180 and the radioactive material 130, such as radioactive iodine $I^{125}$. C.R. Bard manufactures a similar radioactive seed as the STM 1251 $^{125}$I seed. An air gap 190 may be filled with an inert gas, such as argon.

The rod 140 traversing the shell 120 preferably has a nickel layer with a phosphorous content wherein the phosphorous content comprises a level of phosphorous sufficient, when the seed 110 is implanted in tissue, to provide a magnetic resonance image of the seed 110 while substantially eliminating gross artifacts in the magnetic resonance image. For example, the layers of nickel 170 and copper 180 are commonly and preferably plated to the layer of aluminum 160. The electroplating method used to deposit the layer of nickel 170 influences the magnetic characteristics of the rod 140 and therefore affects the visibility of the rod 140 under magnetic resonance imaging (MRI). If the rod 140 is plated using a phosphorous-free bath, the layer of nickel 170 exhibits magnetic characteristics which may cause a relatively large, undesirable artifact on a MRI image of the seed 110. Having such artifacts makes an accurate dosimetry assessment difficult. Undesirable artifacts may further complicate assessments in that they may also distort the gland image.

If the rod 140 is plated using a phosphorous bath, the layer of nickel 170 becomes increasingly non-magnetic as the phosphorous content increases. If the phosphorous content of the layer of nickel 170 becomes great enough, the layer of nickel 170 becomes essentially non-magnetic. The relationship between the level of phosphorous and the magnetic characteristics of nickel are discussed in the *Standard Specification of Autocatalytic (Electroless) Nickel-Phosphorous Phosphorous Coatings on Metal*, published by ASTM International as designation B 733-04, published August 2004, the disclosure of which is hereby incorporated in its entirety by reference. In accordance with an aspect of this invention, the phosphorous content of the layer of nickel 170, and more generally the rod 140, is adjusted to provide enough magnetic character to the seed 110 to allow for imaging and localization, but not enough magnetic character to cause gross artifacts which would interfere with detailed imaging of the prostate gland. Therefore, the electroplating process is used to adjust the phosphorous content of the rod 140 to provide desired magnetic resonance image characteristics.

A method for making the radioactive seed 110 to have desired magnetic characteristics is also provided. The rod 140 is inserted in the shell 120 of the radioactive seed 110. In general, the rod 140 may be exposed to, or submersed in, a nickel-containing bath. The phosphorous present in the bath is incorporated into the nickel layer as it is formed on the rod 120 as it is submersed. As previously explained, the level of phosphorous contained in the nickel layer 170 of rod 140 effects the magnetic characteristics of the rod 140. Therefore, the phosphorus content is adjusted by standard means such that when the seed 110 is placed in tissue and a magnetic resonance image is taken thereof, the level of phosphorous contained in nickel layer 170 of rod 140 is sufficient to substantially eliminate gross artifacts in the magnetic resonance image while providing visibility of the seed 110 on the magnetic resonance image. Adjustment of the phosphorous level in the nickel layer 170 of rod 140 may be made by increasing or decreasing the percentage of phosphorous in the bath or the time the rod 140 is submersed. The level of phosphorous may be adjusted so that visibility of the seed 110 in tissue on a magnetic resonance image is maximized. Determining the proper level of phosphorous may be advantageously determined by any appropriate method. For example, seeds 110 may be manufactured using rods 140 having varying degrees of phosphorus content. The seeds 110 may be inserted into tissue and magnetic resonance images of the seeds 110 may be generated, preferably by MRI. Based on one or more characteristics of the magnetic resonance images, such as the size of artifacts, visibility of the seed 110 and the like, the optimal level of phosphorous in the rods 140 may be determined and optimized seeds produced via the methods disclosed above.

The steps or operations described herein are just exemplary. There may be many variations to these steps or operations without departing from the spirit of the invention. For instance, the steps may be performed in a differing order, or steps may be added, deleted, or modified. The MRI signature of a seed may be varied according to the amount of contained activity (e.g. very radioactive seeds may be made to have larger artifacts than less radioactive seeds, so different activity seeds may be identified during a MRI scan.) Seeds of different MRI visibility may be used in different areas of the prostate, such as having very visible seeds in the interior of the gland and less visible seeds in the periphery of the prostate to minimize interference from the peripheral seeds when imaging the interior of the gland. If the seeds were easily seen on a MRI scan, it may be possible to do the implant without fluoroscopy or CT. In such a case, the seeds would not need a heavy metal gold marker, which would reduce the amount of activity needed in the seeds and therefore reduce cost. By varying the magnetic character of the seeds, it may be possible to move the seeds through an application of an external magnetic field which would permit repositioning after implantation.

In accordance with one embodiment, a method for making a radioactive seed may comprise providing a housing which substantially encloses the radioactive material. The magnetic character of the housing is controlled to obtain a desired magnetic character. A number of methods may be employed to improve, or modify, the magnetic characteristics of the radioactive seed 110. The magnetic character of the radioactive seed may be controlled by varying the metallic composition of the housing, or seed. For example, an amount of iron incorporated into the housing may be varied to provide a desired magnetic character. Types of materials incorporated into the housing may be selected to provide the desired magnetic character to the radioactive seed. For example, one or more types of stainless steel may be selected for incorporation into the housing to provide the desired magnetic character. The magnetic character of the radioactive seed may be controlled via other processes. For example, an iron-containing seed may be subjected to a magnetic field at a predetermined strength for a predetermined time period in order to obtain the desired magnetic character.

By maximizing the visibility of the seed 110 on a magnetic resonance image while minimizing gross artifacts on the image, the MRI may be able to provide both anatomic details and accurate seed position. Accurate mapping of both structure and seed position would possibly allow for definitive post-implant quality control, as well as provide a potential for real-time imaging of the quality of the implant using MRI to the ensure the radiation dose delivered to critical structures around the prostate is minimized. These critical structures, including the penile bulb and neurovascular bundles, are difficult to locate using conventional ultrasound imaging but may be easily viewed using magnetic resonance imaging. Accurate dosimetry can be calculated without the need for (and the inherent error in) fusing two images together. There would therefore likely be no need for a second scan or fusion software. Such accurate imaging further saves time for the patient and the physician and would reduce patient radiation exposure if a post-implant CT is not needed or if fluoroscopy during the procedure is reduced.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. A method of manufacturing brachytherapy seeds such that a difference in the levels of radioactivity of the brachytherapy seeds may be determined by observing the sizes of artifacts produced by the brachytherapy seeds on a magnetic resonance image (MRI) when implanted, each brachytherapy seed comprising a radioactive material, wherein each of a first brachytherapy seed and a second brachtherapy seed comprises a layer of nickel including a level of phosphorus, the method comprising:
    adjusting a first magnetic character of the first brachytherapy seed such that, when viewed on an MRI, the first brachytherapy seed has a first average size of artifact, and adjusting a second magnetic character of the second brachytherapy seed such that, when viewed on an MRI, the second brachytherapy seed has a second average size of artifact different from the first average size of artifact, the first brachytherapy seed being more radioactive than the second brachytherapy seed; and
    adjusting a first level of phosphorus in the layer of nickel of the first brachytherapy seed such that, when viewed on an MRI, the first brachytherapy seed has the first average size of artifact, and adjusting a second level of phosphorus in the layer of nickel of the second brachytherapy seed such that, when viewed on an MRI, the second brachytherapy seed has the second average size of artifact.

2. The method according to claim 1, wherein the first magnetic character and the second magnetic character are adjusted such that the first average size of artifact is larger than the second average size of artifact.

3. The method according to claim 1, wherein both the first magnetic character and the second magnetic character are adjusted to be strong enough to provide a magnetic resonance signature that helps define the seed position in a magnetic resonance image, but not so strong as to undesirably distort the image of a body region.

4. The method according to claim 1, wherein neither the first brachytherapy seed nor the second brachytherapy seed includes a gold marker.

5. The method according to claim 1, further comprising enclosing radioactive material of the first brachytherapy seed in a first shell or housing and enclosing radioactive material of the second brachytherapy seed in a second shell or housing.

6. The method according to claim 5, wherein the first shell or housing encloses an internal metal structure comprising a gold core and layers of aluminum and copper, and wherein enclosing the radioactive material of the first brachytherapy seed in the first shell or housing includes enclosing both the radioactive material of the first brachytherapy seed and the internal metal structure in the first shell or housing.

7. The method according to claim 5, further comprising forming a first air gap between the radioactive material of the first brachytherapy seed and the first shell or housing, and forming a second air gap between the radioactive material of the second brachytherapy seed and the second shell or housing.

8. The method according to claim 7, further comprising filling the first air gap formed between the radioactive material of the first brachytherapy seed and the first shell or housing with an inert gas, and filling the second air gap formed between the radioactive material of the second brachytherapy seed and the second shell or housing with an inert gas.

9. The method according to claim 1, wherein the first level of phosphorus and the second level of phosphorus are adjusted such that the first average size of artifact is larger than the second average size of artifact.

10. The method according to claim 1, wherein the layer of nickel of the first brachytherapy seed is coated on a first internal metal structure, and wherein the radioactive material of the first brachytherapy seed and the first internal metal structure are enclosed in a first shell or housing.

11. The method according to claim 10, wherein the first internal metal structure includes a layer of aluminum and a layer of copper, and wherein the layer of nickel of the first brachytherapy seed is disposed between the layer of aluminum and the layer of copper, and the radioactive material of the first brachytherapy seed is disposed on the layer of copper.

12. The method according to claim 1, wherein the radioactive material of the first brachytherapy seed is radioactive iodine.

13. The method according to claim 1, wherein the layer of nickel including phosphorus of the first brachytherapy seed is non-radioactive, and the layer of nickel including phosphorus of the second brachytherapy seed is non-radioactive.

14. The method according to claim 1, wherein the first brachytherapy seed and the second brachytherapy seed include iron, and further comprising subjecting the first brachytherapy seed to a first magnetic field at a first predetermined strength to obtain the first magnetic character, and subjecting the second brachytherapy seed to a second magnetic field at a second predetermined strength to obtain the second magnetic character.

15. A method of brachytherapy treatment, comprising:
    implanting in a patient a first brachytherapy seed having a first magnetic character configured to produce a first average size of artifact on a magnetic resonance image (MRI) corresponding to a first radioactivity level of the first brachytherapy seed, wherein the first magnetic character is configured to produce the first average size of artifact on a MRI by the inclusion, in the first brachytherapy seed, of a first layer of nickel including a first level of phosphorus, the first level of phosphorus in the first layer of nickel having been selected to produce the first average size of artifact;

implanting in the patient a second brachytherapy seed having a second magnetic character configured to produce a second average size of artifact on a MRI corresponding to a second radioactivity level of the second brachytherapy seed, wherein the second average size of artifact is different from the first average size of artifact, and the first radioactivity level is different from the second radioactivity level;

viewing the implanted first brachytherapy seed and the implanted second brachytherapy seed on a post-implantation MRI; and identifying which brachytherapy seed is the first brachytherapy seed with the first radioactivity level and which brachytherapy seed is the second brachytherapy seed with the second radioactivity level by comparing the first average size of artifact to the second average size of artifact on the post-implantation MRI.

16. The method according to claim 15, wherein the second magnetic character is configured to produce the second average size of artifact on a MRI by the inclusion, in the second brachytherapy seed, of a second layer of nickel including a second level of phosphorus, the second level of phosphorus in the second layer of nickel having been selected to produce the second average size of artifact.

17. A method of manufacturing brachytherapy seeds such that a difference in the levels of radioactivity of the brachytherapy seeds may be determined by observing the sizes of artifacts produced by the brachytherapy seeds on a magnetic resonance image (MRI) when implanted, each brachytherapy seed comprising both a radioactive material and iron, the method comprising:

adjusting a first magnetic character of a first brachytherapy seed such that, when viewed on an MRI, the first brachytherapy seed has a first average size of artifact, and adjusting a second magnetic character of a second brachytherapy seed such that, when viewed on an MRI, the second brachytherapy seed has a second average size of artifact different from the first average size of artifact, the first brachytherapy seed being more radioactive than the second brachytherapy seed; and subjecting the first brachytherapy seed to a first magnetic field at a first predetermined strength to obtain the first magnetic character, and subjecting the second brachytherapy seed to a second magnetic field at a second predetermined strength to obtain the second magnetic character.

* * * * *